United States Patent
Pacheco et al.

(10) Patent No.: US 9,291,576 B2
(45) Date of Patent: Mar. 22, 2016

(54) DETECTION OF DEFECT IN DIE

(71) Applicant: Intel Corporation, Santa Clara, CA (US)

(72) Inventors: Mario Pacheco, Tempe, AZ (US); Deepak Goyal, Phoenix, AZ (US)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 14/329,686

(22) Filed: Jul. 11, 2014

(65) Prior Publication Data

US 2016/0011122 A1    Jan. 14, 2016

(51) Int. Cl.
| | | |
|---|---|---|
| *G01J 4/00* | (2006.01) | |
| *G01N 21/95* | (2006.01) | |
| *H01L 21/67* | (2006.01) | |
| *G01N 21/88* | (2006.01) | |
| *G01N 21/21* | (2006.01) | |

(52) U.S. Cl.
CPC ............ *G01N 21/9505* (2013.01); *G01N 21/21* (2013.01); *G01N 21/8806* (2013.01); *H01L 21/67288* (2013.01); *G01N 2201/0612* (2013.01)

(58) Field of Classification Search
CPC ....... B23K 26/08; G01N 21/00; G01N 21/85; H01S 3/091; A61B 3/14; G06K 9/00
See application file for complete search history.

(56) References Cited

U.S. PATENT DOCUMENTS

| | | | | |
|---|---|---|---|---|
| 4,386,854 A | * | 6/1983 | Byer ....................... | G01S 17/89 250/338.5 |
| 6,215,892 B1 | * | 4/2001 | Douglass ............... | G01N 1/312 382/128 |
| 6,438,256 B1 | * | 8/2002 | Rubin .................... | G01N 21/53 358/448 |
| 2004/0233962 A1 | * | 11/2004 | Reid ....................... | H01S 5/187 372/75 |
| 2005/0279736 A1 | * | 12/2005 | Bruland ............. | B23K 26/0613 219/121.8 |
| 2007/0210269 A1 | * | 9/2007 | Sonehara ........... | G01N 21/0303 250/576 |
| 2014/0268039 A1 | * | 9/2014 | Arianta ................... | A61B 3/102 351/206 |

* cited by examiner

*Primary Examiner* — Tarifur Chowdhury
*Assistant Examiner* — Jamil Ahmed
(74) *Attorney, Agent, or Firm* — Schwegman Lundberg & Woessner, P.A.

(57) ABSTRACT

Generally discussed herein are systems, apparatuses, and methods that can detect a defect in a die. According to an example, a method can include transmitting a first beam of light with a wavelength and optical power configured to produce a reflected beam with at least one milli-Watt of power, linearly polarizing the first beam of light in a specific direction, circularly polarizing the linearly polarized light by a quarter wavelength to create circularly polarized light, directing the circularly polarized light to a device under test, linearly polarizing light reflected off the device under test by a quarter wavelength, or creating an image of the linearly polarized light reflected off the device under test.

21 Claims, 3 Drawing Sheets

DETECTION OF DEFECT IN DIE

TECHNICAL FIELD

Examples generally relate to detecting a defect in a die. One or more examples can help provide the ability to detect a defect internal to the die.

TECHNICAL BACKGROUND

Substrate or die manufacturing processes can include etching, cutting, deposition, or other processes. Die manufacturing processes are often quite complicated and there are some variations in the manufacturing process. Some defects can be patent or latent. Some defects can be formed in a die during the manufacturing process and some defects be formed in the die after the die has completed the manufacturing process, such as after the die is being used by an end user.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DESCRIPTION OF EMBODIMENTS

Figure 1:
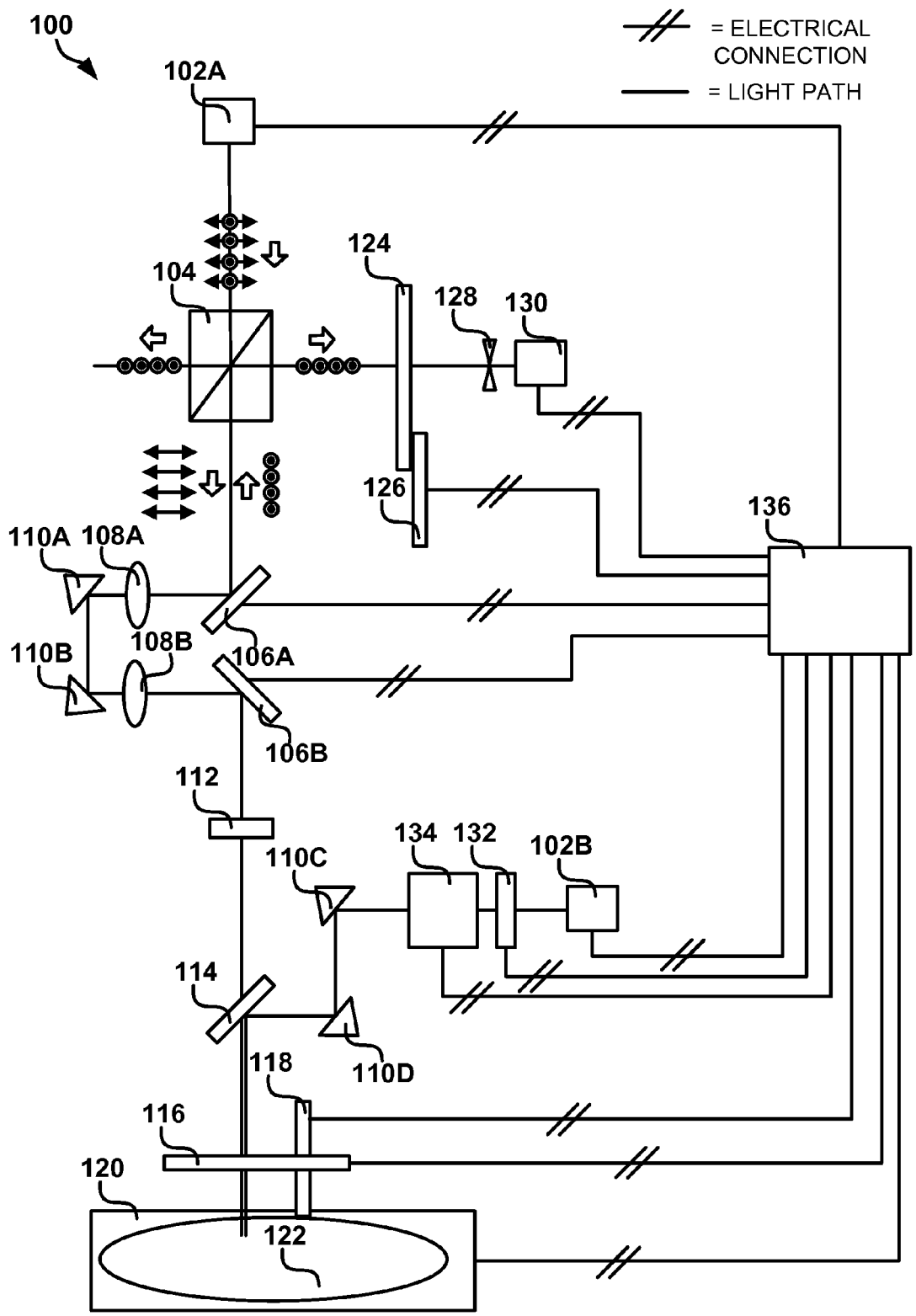
FIG. 1 shows a block diagram of an example of a system, according to one or more embodiments.

Examples in this disclosure relate generally to detecting a defect in a die (e.g., silicon or other semiconductor die).

Methods, systems, or apparatuses in accord with this disclosure can help fill a metrology gap in detecting die defects, such as a defect that is invisible to conventional imaging methods (e.g., optical, x-ray, electron, or acoustic imaging).

Defects created during a wafer etching process are particularly troublesome. For example, the defect can include a hole or pit defect left on a metal layer, such as at or around a wafer street. The wafer street is the space that separates dice on the wafer from each other. The defect can tend to appear in a limited number of areas, and due, at least in part, to lack of proper characterization metrology, it is difficult to predict where such defects will form or determine where they have formed.

Once the wafer layers are completely built, the etching defects are invisible from the backside of the wafer due to the opaque nature of the wafer (e.g., a silicon wafer, such as a heavily doped silicon wafer). It can be difficult to detect such defects until the silicon is fully assembled and the packaged die fails electrically during test. The die can fail because die cracking or delamination has propagated to an electrical metal structure.

No known, time-efficient metrology to inspect either a full wafer before dicing or incoming silicon die before assembly exists in the semiconductor industry. This metrology gap represents millions of dollars lost in the assembling of bad silicon dies that have undetected etching defects. Adjusting the chemical etching instrumentation process so that such defects are not created, can benefit from a metrology that is capable of detecting these defects. This disclosure addresses such a metrology gap.

A previous method for detection or inspection of etching or pitting defects in die wafers involves a tedious and time consuming procedure that includes dicing the wafer and then mechanically thinning a backside of a die to be inspected down to about a few microns so that it can be inspected by traditional near infrared microscopy techniques. This thinning is because the die is generally opaque to visible wavelengths and almost opaque to traditional near infrared imaging, so the defects are hidden if the die is not thinned down. This procedure consumes several days per die and can only be done on limited, selected die (e.g., a random or periodized selection) due to its time consuming nature. Another option is visual inspection of metal layers during the etching process, however this test method can be time and resource intensive.

In addition to a defect that can occur before dicing the die from the wafer, a defect can occur during or after dicing the die from the wafer. A laser scribing or sawing process to dice a wafer has the potential of creating an internal micro crack in the die, such as at a location in or around the laser trench region. Such a micro cracking defect can propagate to an active layer of the die, such as during the assembly process. Depending on several factors, such as size, stress distribution, assembly process, among others, this kind of defect can have the potential to produce a functional failure. Monitoring the location and dimensions of such defects can help quality control in process development as well as manufacturing.

The trench created by a laser scribing process is typically filled with an ablation recast, which can hinder the possibility of a visual inspection from an external side of the trench. Also, the micro crack can propagate internal to the die, further hindering detectability of the existence and dimensions of the micro crack. A laser induced micro crack can be embedded inside a die that is opaque to visible light. Current optical inspection technology may not be sufficient to detect them.

The lack of availability of capable metrology to detect a micro crack in a time efficient and nondestructive manner exposes a current metrology gap.

The previous metrology for detection or inspection of a laser scribe induced die micro crack can include one or more limitations. A current metrology includes the use of Focused Ion Beam (FIB) milling with Scanning Electron Microscopy (SEM) imaging to obtain a physical cross section of a laser trench area. The cross section is generally of a randomly picked single location along the trench. This method consumes several hours to obtain one single cross section. The accuracy can be relatively poor due to the limited nature of the cross section and the randomness of the location's selection. In using this method, there is no guarantee that a cross section showing no cracking defects means that there is no such defect at another location.

Another limitation of the FIB SEM method is that it is performed with a diced die, and it generally cannot be performed with a packaged die or full wafer, due to sample size restrictions in the FIB SEM system. This restriction of the FIB SEM system can create additional time consuming sample preparation required to be done prior to FIB SEM processing.

This disclosure addresses a problem discussed by enabling the inspection of a die from the wafer backside and by rendering information and quantification of such defects, such as without needing to thin the silicon die. An entire wafer can be inspected without wafer or die thinning or assembling the die, thus providing a faster detection capability.

This disclosure addresses such an analytical metrology gap. An advantage of a method, apparatus, or system in accord with this disclosure can include analyzing a die for defects in less time (e.g., detecting in a few minutes or seconds compared to several hours) or more accurately than previous metrology (e.g., since an entire die edge can be scanned and its image can be digitally processed for automated defects localization and quantification as compared to a random FIB SEM cross section).

Embodiments discussed herein can provide a faster, non-destructive metrology (i.e. one that does not require die thinning) that can deliver information about the existence or non-existence of a micro size defect in a die, such as along a street of a wafer or along the edge of the die. Embodiments discussed herein can provide an X, Y, or Z localization and quantification for a diced die, fully assembled or packaged die, or a die on a wafer. Embodiments discussed herein can help improve yield or ramp.

Reference will now be made to the FIGS. to describe details of one or more embodiments.

FIG. 1 shows an example of a system 100 for detecting defects in a die, according to one or more embodiments. The system 100 can include one or more light emitting elements 102A or 102B (e.g., a laser diode), a beam splitter 104, one or more galvanometers 106A or 106B, one or more lenses 108A or 108B, or one or more redirecting mirrors 110A, 110B, 110C, or 110D. The system 100 can include a quarter wave plate 112, a dichroic mirror 114, an objective lens set exchanger 116, a Z-axis stage 118, an XY-axis stage 120, or a wafer or die under test 122. The system 100 can include a set of filters 124 (e.g., an optical density filter), a stage 126, an aperture 128, or a photo detector 130. The system 100 can include an optical offset element 132, an auto focus element 134, or a controller 136.

A summary of the operation of the system 100 is followed by a more detailed description of the elements of the system 100. The light emitting element 102A can transmit Near Infrared (NIR) radiation with a wavelength peak specifically selected for the wafer or die under test 122. The NIR beam can be sent through the polarizing beam splitter 104 and the reflected signal can be blocked to cancel, while the transmitted linearly polarized beam is directed onto a Front Surface Mirror (FSM) mounted on a resonant X-axis galvanometer 106A, which redirects the beam to travel through an optical beam collimator that refocuses the beam onto a second FSM mounted on a Y resonant galvanometer 106B. This linearly polarized and XY oscillating beam can pass through the quarter wave plate 112 that shifts the polarization axis by a quarter wavelength, thus creating circularly polarized light. This beam is then passed through the dichroic mirror 114 (later used for autofocusing purposes) that can operate at a wavelength located in the green side of the optical spectrum so that it does not affect the intensity of the NIR beam. An objective lens of the lens set exchanger 116 can be used to focus the beam on the surface of the wafer or die under test 122. An automated linear stage (e.g., the Z-axis stage 118) can be used to adjust the objective lens position via the controller 136, which can be coupled to a computer. The objective lens can be mounted in the lens exchanger 116 (e.g., turret) to allow for the exchange between different magnification lenses.

The NIR beam can be back reflected and back scattered by the wafer or die under test 122, and the net beam can be sent back through the same optical path through which it came. When the beam passes through the quarter wave plate 112 for the second time, the beam's polarization axis shifts again, thus resulting in a beam that is linearly polarized perpendicular to the beam transmitted by the beam splitter 104. This polarization axis rotated beam continues traveling to be reflected by the FSMs on the X and Y galvanometers 106A and 106B until it reaches the polarizing beam splitter 104, which selectively reflects this polarization axis. The beam is then sent to pass through the optical set of filters 124 and the aperture 128 before reaching the end of the optical path at the photo detector 130.

The light emitting element 102A-B can produce coherent light, such as laser light. Laser light is optically amplified light. The laser light can be spatially or temporally coherent. Spatial coherence is sometimes referred to as collimated and can allow a light to travel over longer distances without spreading. Temporal coherence can allow the light to include few frequencies (e.g., to have a single color of light). In one or more embodiments, the light emitting element 102A-B can include a laser diode. A laser diode includes a P-i-N diode and has an active intrinsic region. Electrons and holes can be provided to the P and N regions, respectively to make the P-i-N region conduct.

The light from the light emitting element 102A-B can be polarized in one or more directions. In FIG. 1 the opposite, opposing arrows on or near the light path indicate a first direction of polarization and the partially filled circles indicate a second direction of polarization orthogonal to the first direction of polarization.

The light emitting element 102A can be configured to transmit light of a specific wavelength or at a specific optical intensity. The wavelength can be determined by passing a broadband optical beam through bulk silicon (e.g., a die that has metal layers removed) and measuring the transmitted beam, such as with an optical spectrum analyzer. The wavelength of light at the peak of the transmitted beam can indicate a wavelength of light that passes through the die with less loss as compared to the remaining wavelengths. In one or more embodiments, the wavelength of light transmitted by the light emitting element 102A can be between about 900 and 1500 nanometers. In one or more embodiments, the wavelength of light transmitted by the light emitting element 102A can be between about 1000 and 1350 nanometers. In one or more embodiments, the wavelength of light transmitted by the light emitting element can be between about 1100 and 1250 nanometers. In one or more embodiments, the wavelength of light transmitted by the light emitting element can be between about 1150 and 1200 nanometers (e.g., 1175 nanometers plus or minus 25 nanometers). In one or more embodiments, the wavelength of light transmitted by the light emitting element can be between about 1175 and 1225 nanometers (e.g., 1200 nanometers plus or minus 25 nanometers).

The optical intensity at which the light emitting element 102A transmits can be determined by transmitting different optical intensity beams, such as at the wavelength determined as discussed herein, onto dies of varying thicknesses and measuring the transmitted power. The optical intensity is directly proportional to the transmitted power. The transmitted power decreases as the die thickness increases. The transmitted power generally decreases as the doping of the die increases. Thus, the thicker the die the greater the optical intensity required to attain a threshold transmitted power (and optical intensity). Typical, currently available, commercial photo detectors require about a one milli-Watt transmit power to produce an image.

For example, the light produced by the light emitting element 102A can have a power of about 200 milli-Watts to generate a transmitted light of about one milli-Watt when the light is incident upon a heavily doped die that is about 800 micrometers thick. In another example, the light produce by the light emitting element 102A can have a power of about 100 milli-Watts to produce a one milli-Watt transmission signal when the light is incident upon a heavily doped die that is about 500 micrometers thick. In yet another example, the light produce by the light emitting element 102A can have a power of about 10 milli-Watts to produce a one milli-Watt transmission signal when the light is incident upon a heavily doped die that is about 200 micrometers thick.

The beam splitter 104 can receive light from the light emitting element 102A-B and split the light into two or more beams of light. The light beams emitted can include different polarizations, such as the first direction of polarization and the second direction of polarization.

In the example shown in FIG. 1 the light beam with the first direction of polarization is emitted through the beam splitter 104 to a first galvanometer 106A. The galvanometer 106A can be configured to move along a first axis that is orthogonal to a direction that the galvanometer 106B is configured to move. The galvanometer 106A-B can provide a light steering mechanism, such as to redirect the light emitted from the beam splitter 104. Light reflected off a mirror mounted on the galvanometer 106A can be oscillating in the X direction and light reflected off a mirror mounted on the galvanometer 106B can be oscillating in the Y direction. A light beam that has been incident on both a mirror mounted on the galvanometer 106A and a mirror mounted on the galvanometer 106B can be oscillating in both the X and Y directions.

The combination of the lens 108A-B and the mirrors 110A-B can function as an optical beam collimator that refocuses the light onto a mirror mounted on a Y resonant galvanometer 106B.

The quarter wave plate 112 can receive a light beam and produce a light beam that includes a phase shift different from the received light beam. In one or more embodiments, the produced light beam includes a phase shift of a quarter wavelength from the received light beam (i.e. the wave plate is a quarter-wave plate).

The light from the quarter wave plate 112 can be received at the dichroic mirror 114. The dichroic mirror 114 can allow received light that does or does not have a specific wavelength there through. The dichroic mirror 114 can reflect light that is of a specific frequency, such as to redirect the light with the specific frequency.

Light from the quarter wave plate 112 can be received by the lens exchanger 116. The lens exchanger 116 can include a plurality of objective lenses configured to help focus reflected light from the wafer or die under test 122 so as to produce a real image. The lens exchanger 116 can be mechanically coupled to the Z-axis stage 118. The Z-axis stage 118 can move an objective lens of the lens exchanger closer or further from the wafer or die under test 122. Such a configuration can allow an image of varying depths of the wafer or die under test 122 to be produced. Producing such an image can help in detecting a defect in the wafer or die under test 122 that is around the active area thereof. Cracks or other defects in the wafer or die under test 122 can propagate to locations away from the active area, and the Z-axis stage 118 can help produce an image of such a defect.

The XY-axis stage 120 can provide the ability to move the wafer or die under test 122 in the XY plane or along the X or Y axes. A different location of the wafer or die under test 122 can be imaged by moving the XY-axis stage 120.

Light reflected from the die or wafer under test 122 can be reflected toward the object lens of the lens exchanger 116. The objective lens can focus the reflected light into a real image. The light from the object lens can be received at the dichroic mirror 114, which will filter out light of a certain wavelength and allow light that does not include the filtered out wavelength there through. This light is received by the quarter wave plate 112, which shifts its polarization axis, creating linearly polarized light thereon. Note that light that is reflected by the wafer or die under test 122 has been linearly polarized by the quarter wave plate once before being reflected. The reflected light that passes through the dichroic mirror 114 will be polarized again by the quarter wave plate 112. Thus, using a quarter-quarter wave plate 112, as in the example of FIG. 1, the light will be polarized to be generally orthogonal from the polarization the light had when it was first incident on the quarter wave plate 112. This is indicated by the opposite opposing arrows and the partially filled circles leaving and coming towards the beam splitter 104, respectively.

This polarized light from the quarter wave plate 112 can be reflected towards the beam splitter 104. The polarized light can be reflected by the beam splitter 104 towards the optical set of filters 124. The optical set of filters 124 can include a neutral density filter that has a constant attenuation across wavelengths (e.g., visible light) incident thereon. The optical set of filters 124 can include a variable intensity filter, such as to include a variety of optical densities. The greater the optical density of the portion of the optical set of filters 124 the light is incident on, the more attenuated the light incident thereon becomes. A variable optical set of filters 124 can include a first optical density at a first portion thereof, and a second different optical density at a different portion of thereof. More optical densities can be used. The density of the optical set of filters 124 can be chosen, such as by moving the optical set of filters 124 using the stage 126. By moving the optical set of filters 124 a different portion of the optical set of filters 124 can receive the light from the beam splitter 104 and the light incident upon the optical set of filters 124 can be attenuated in accord with the optical density corresponding to that portion of the optical set of filters 124.

The light from the optical set of filters 124 can be received at the aperture 128. The aperture can include an iris pinhole. The aperture 128 can be configured to filter out back reflection and backscattering of light from the wafer or die under test 122. Selective NIR light (e.g., radiation) from a point or plane of interest (e.g., the focal point or plane) can be transmitted through the aperture 128. The aperture can be used to remove a reflection coming from a backside of the wafer or die under test 122 backside or backscattering of light produced by wafer or die under test 122 doping material.

The light from the aperture 128 can be transmitted to the photo detector 130. The photo detector 130 can produce an electrical signal in response to light incident thereon. The electrical signal can include different properties (e.g., frequency, magnitude, phase, etc.) depending on the frequency or intensity of the light incident thereon. The electrical signals created can help produce a digital rendering of the wafer or die under test 122 at or around a location the light is incident thereon.

Using light with a high level of optical power when imaging a thin or lightly doped die, poses the risk of damaging the photo detector 130. To mitigate this, the optical set of filters 124 (e.g., variable filter) can be mounted on the stage 126 in such a way that it provides an attenuation of the optical power to protect the photo detector 130.

A stress induced defect in the wafer or die under test 122 can be detected by using a polarizing beam splitter combined with a wave plate that delays the light incident thereon in such a way so as to make a localized variation in index of refraction created by a defect in the wafer or the die under test 122 modulate the intensity of the back reflected signal.

Granular noise in images can be filtered by collecting a specified number of images of the same general location and averaging the pixel values of the images that correspond to the same location.

The second light emitting element 102B can transmit light through the optical offset element 132 and the auto focus element 134. The optical offset element 132 can be used to help focus the light from the light emitting element 102B onto a location of interest in the Z-axis direction. In an example where a plane of interest and the backside or surface of the die under test 122 do not include the same location along the Z-axis direction, the auto focus element 134 can track the backside of the wafer, while the optical offset element 132 introduces a Z shift such that the objective lens focuses at a different location in the Z-axis direction (e.g., where the metals of the die under test 122 is located). Such variability can help in imaging a warped wafer or die. Such variability can help accommodate a variety of die thicknesses and distances to the location of interest (e.g., the location of the wafer or die in the Z-axis direction that is to be imaged). The auto focus element 134 can help track a surface of the silicon die that is facing the XY-stage 120.

Certain defects, such as die edge cracking or a conductor delamination, can propagate a distance (e.g., up to a few microns) in the Z-axis direction. Collecting images above and below a plane of interest and combining the images in a single overlaid image can help reveal more information than a single image taken at the plane of interest. The fingerprint of a specific defect depends on a number of planes that the defect intersects, a spacing between the planes, or Z-axis direction distance above and below the plane of interest.

The controller 136 can be electrically coupled to the light emitting elements 102A-B, the photo detector 130, the stage 126, the galvanometers 106A-B, the optical offset element 132, the auto focus element 134, the Z-axis stage 118, the lens exchanger 116, or the XY stage 120. The controller 136 can be coupled to a computer (e.g., the computing device shown in FIG. 3). The controller 136 can provide an interface to each of the elements it is electrically coupled to, such as to provide an automated system or process for detecting a defect in the die or wafer under test 122.

The controller 136 can transmit a control signal to the light emitting element 102A-B, such to cause the light emitting element to adjust a wavelength or intensity of light emitted therefrom. The controller 136 can receive data from the photo detector that corresponds to an image detected by the photo detector 130. The controller 136 can analyze the image to determine if the image indicates that a defect is present in the wafer or die under test 122.

The controller 136 can transmit a signal to the stage 126, the Z-axis stage 118, or the XY stage 120 that causes the stage to move a specified distance or a specified direction. The controller 136 can transmit a signal to the galvanometer 106A-B that causes a frequency of oscillation of the galvanometer to be adjusted. The controller 136 can transmit a signal to the optical offset element 132 that causes the offset element 132 to adjust a location in the Z-axis direction that the light from the light emitting element 102B is focused on. The controller 136 can transmit a signal to the auto focus element 134 to adjust the focus of the light from the optical offset element. The controller 136 can transmit a signal to the lens exchanger 116 that causes a different objective lens to be in the optical path of light from the light emitting element 102A.

Figure 2:
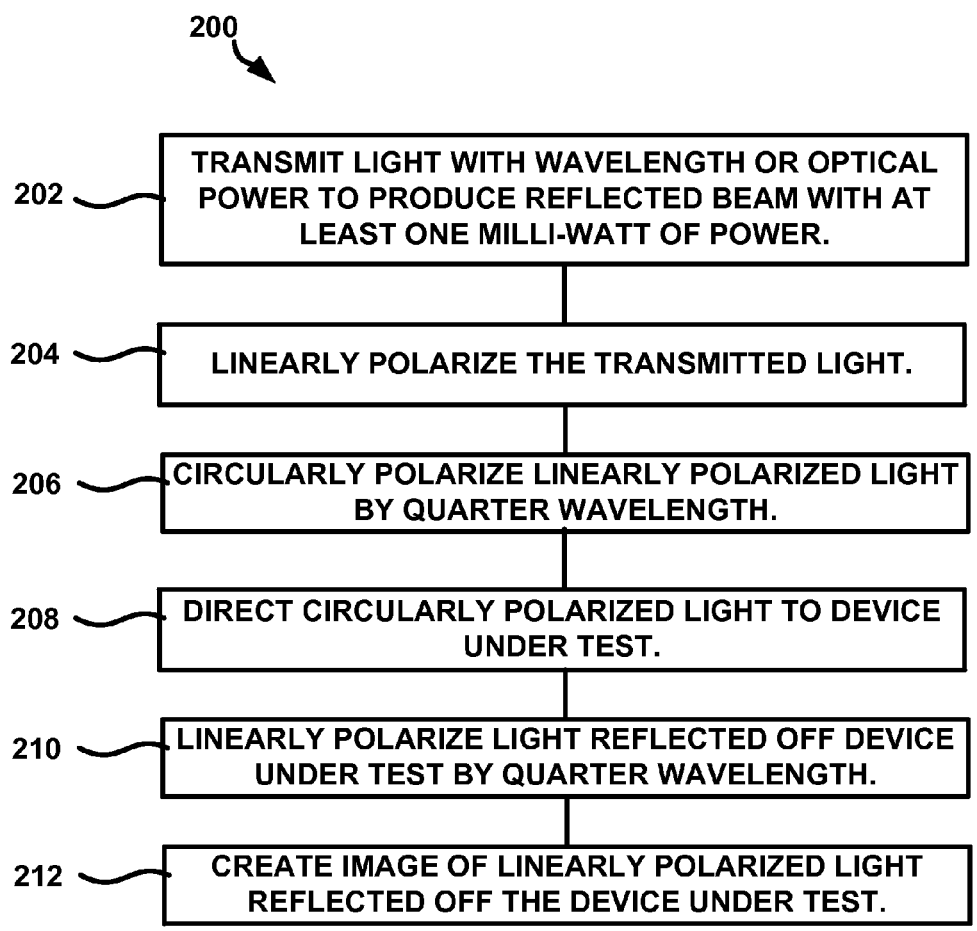
FIG. 2 shows a flow diagram of an example of a technique, according to one or more embodiments.

FIG. 2 shows a flow diagram of an example of a technique 200, according to one or more embodiments. The technique 200, as illustrated includes: transmitting light with a wavelength or optical power to produce a reflected beam with at least one milli-Watt of power at operation 202; linearly polarizing the transmitted light at operation 204; circularly polarizing the linearly polarized light by a quarter wavelength at operation 206; directing circularly polarized light to device under test at operation 208; linearly polarizing light reflected off device under test by quarter wavelength at operation 210; and creating an image of the linearly polarized light reflected off the device under test at operation 212.

The operation at 202 can include transmitting a beam of light produced by a laser, such as a laser diode. The operation at 202 can include transmitting the first beam of light includes transmitting the first beam of light at a wavelength of between about 1150 and 1200 nanometers. The operation at 202 can include transmitting the first beam of light includes transmitting the first beam of light at a power of about 200 milli-Watts or greater power.

The operation at 204 can be performed by a polarizing beam splitter, for example. The beam splitter can allow light that is polarized in a specific direction to pass there through and can cancel light that is not polarized in the specific direction.

The technique 200 can include an operation to collimate the polarized light before polarizing the polarized light by a quarter wavelength. Collimating the polarized light can include oscillating the polarized light in a first direction and oscillating the polarized light in a second direction orthogonal to the first direction to oscillate the polarized light in the first and second directions. The technique 200 can include filtering the half wavelength polarized light using a neutral density filter before creating the image at operation 212. The technique 200 can include filtering out a back reflection and a backscattering of light from light reflected off the device under test. The technique 200 can include transmitting a second beam of light, or adjusting a focal point of the second beam of light to a specific depth on the device under test.

Figure 3:
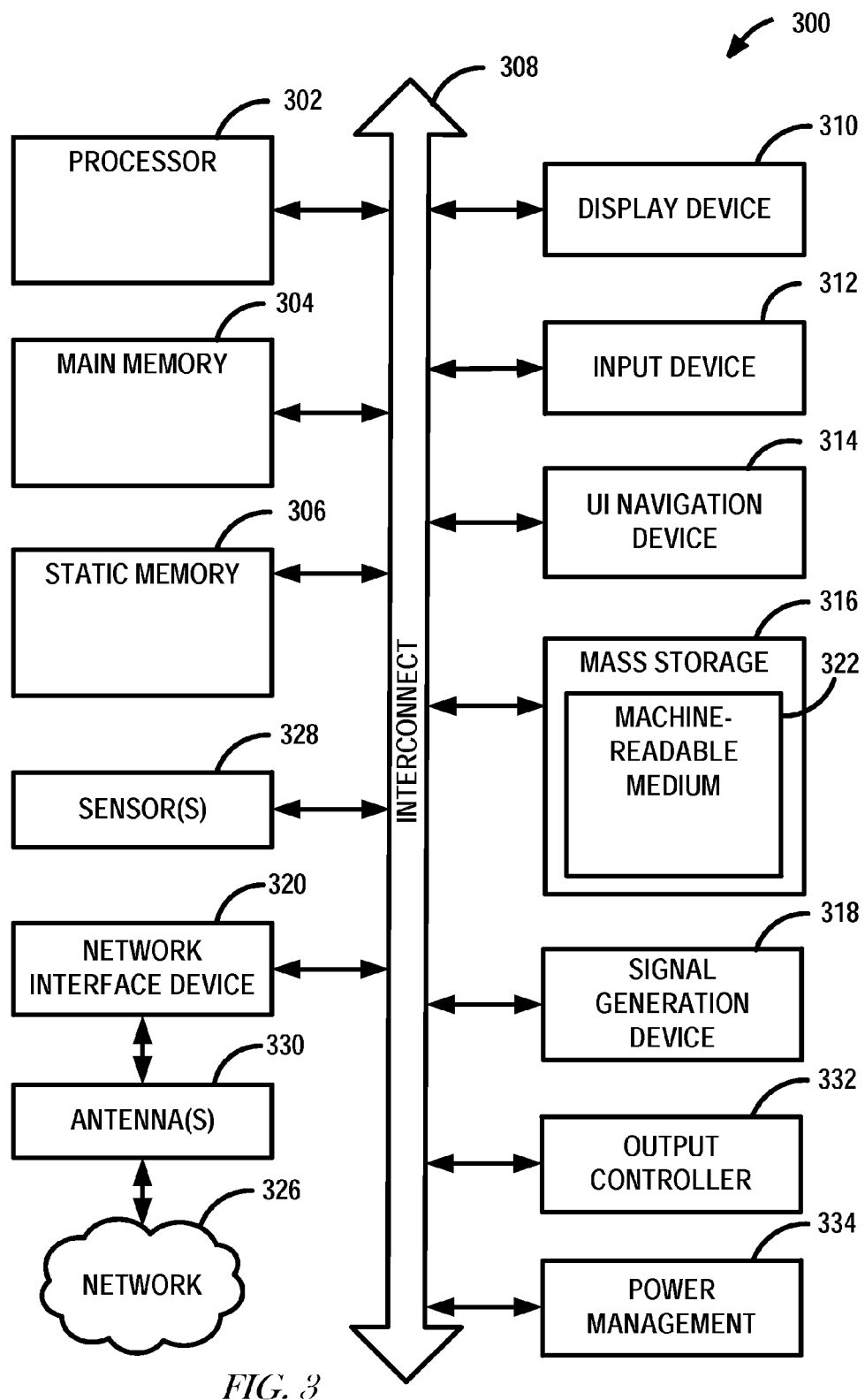
FIG. 3 shows an example of a computer system.

FIG. 3 is a block diagram illustrating an example computer system 300 machine which can be coupled to the controller 136. The controller 136 can include one or more of the components of the computer system 300, so as to help the controller 136 carry out its operations. Computer system 300 can be a computing device. In an example, the machine can operate as a standalone device or can be connected (e.g., via a cellular network) to other machines. In a networked deployment, the machine can operate in the capacity of either a server or a client machine in server-client network environments, or it can act as a peer machine in peer-to-peer (or distributed) network environments. Further, while only a single machine is illustrated, the term "machine" shall also be taken to include any collection of machines that individually or jointly execute a set (or multiple sets) of instructions to perform any one or more of the methodologies discussed herein.

Example computer system 300 can include a processor 302 (e.g., a Central Processing Unit (CPU), a Graphics Processing Unit (GPU) or both), a main memory 304 and a static memory 306, which communicate with each other via an interconnect 308 (e.g., a link, a bus, etc.). The computer system 300 can further include a video display unit 310, an alphanumeric input device 312 (e.g., a keyboard), and a User Interface (UI) navigation device 314 (e.g., a mouse). In an example, the video display unit 310, input device 312 and UI navigation device 314 are a touch screen display. The computer system 300 can additionally include a storage device 316 (e.g., a drive unit), a signal generation device 318 (e.g., a speaker), an output controller 332, a power management controller 334, and a network interface device 320 (which can include or operably communicate with one or more antennas 330, transceivers, or other wireless communications hardware), and one or more sensors 328, such as a GPS sensor, compass, location sensor, accelerometer, or other sensor. The antennas 330 can be coupled to a network 326. Any of the items of the system 300 can include a substrate that was built on a panel discussed herein.

EXAMPLES AND NOTES

The present subject matter may be described by way of several examples.

Example 1 can include or use subject matter (such as an apparatus, a method, a means for performing acts, or a device readable memory including instructions that, when performed by the device, can cause the device to perform acts), such as can include or use (1) a light emitting element configured to transmit light with a wavelength and optical power configured to produce a reflected beam with at least one milli-Watt of power, (2) a polarized beam splitter to receive the transmitted light from the light emitting element and transmit light that is linearly polarized in a specific direction, (3) a quarter wave plate to receive the polarized light from the beam splitter, circularly polarize the light incident thereon by a quarter wavelength, transmit the quarter wavelength polarized light, receive quarter wavelength polarized light reflected from a device under test, linearly polarize the received quarter wavelength polarized light by another quarter wavelength to create half wavelength polarized light, and transmit the half wavelength polarized light, or (4) a photo detector to receive half wavelength light transmitted by the quarter wave plate.

Example 2 can include or use, or can optionally be combined with the subject matter of Example 1 to include or use, a collimator situated between the beam splitter and the quarter wave plate to collimate the linearly polarized light from the beam splitter.

Example 3 can include or use, or can optionally be combined with the subject matter of Example 2 to include or use, wherein the collimator comprises a first front surface mirror mounted on a first galvanometer configured to oscillate the first front surface mirror in a first direction and a second front surface mirror mounted on a second galvanometer configured to oscillate the second front surface mirror in a second direction orthogonal to the first direction so that light incident on the first and second front surface mirrors oscillates in the first and second directions.

Example 4 can include or use, or can optionally be combined with the subject matter of at least one of Examples 1-3 to include or use a variable optical density filter situated between the beam splitter and the photo detector, wherein the filter is situated on a stage configured to change the position of the optical density filter so as to selectively change an optical density of the filter in the path of the light from the beam splitter.

Example 5 can include or use, or can optionally be combined with the subject matter of at least one of Examples 1-4 to include or use a second light emitting element configured to transmit a second beam of light, or an auto focus element configured to receive the second beam of light and focus the second beam of light at a specific depth in the device under test.

Example 6 can include or use, or can optionally be combined with the subject matter of at least one of Examples 1-5 to include or use, wherein the first light emitting element is configured to transmit light at a wavelength of between about 1150 and 1200 nanometers.

Example 7 can include or use, or can optionally be combined with the subject matter of at least one of Examples 1-6 to include or use, wherein the first light emitting element is configured to transmit light at a power of about 200 milli-Watts or greater.

Example 8 can include or use, or can optionally be combined with the subject matter of at least one of Examples 1-7 to include or use an aperture situated between the beam splitter and the photo detector to filter out back reflection and backscattering of light from the device under test.

Example 9 can include or use subject matter (such as an apparatus, a method, a means for performing acts, or a device readable memory including instructions that, when performed by the device, can cause the device to perform acts), such as can include or use (1) transmitting a first beam of light with a wavelength and optical power configured to produce a reflected beam with at least one milli-Watt of power, (2) linearly polarizing the first beam of light in a specific direction, (3) circularly polarizing the linearly polarized light by a quarter wavelength to create circularly polarized light, (4) directing the circularly polarized light to a device under test, (5) linearly polarizing light reflected off the device under test by a quarter wavelength, or (6) creating an image of the linearly polarized light reflected off the device under test.

Example 10 can include or use, or can optionally be combined with the subject matter of Example 9 to include or use collimating the linearly polarized light before circularly polarizing the polarized light by a quarter wavelength.

Example 11 can include or use, or can optionally be combined with the subject matter of Example 10 to include or use, wherein collimating the linearly polarized light includes oscillating the linearly polarized light in a first direction and oscillating the linearly polarized light in a second direction orthogonal to the first direction to oscillate the linearly polarized light in the first and second directions.

Example 12 can include or use, or can optionally be combined with the subject matter of at least one of Examples 9-11 to include or use filtering the linearly polarized light reflected off the device under test using a variable neutral density filter before creating the image.

Example 13 can include or use, or can optionally be combined with the subject matter of at least one of Examples 9-12 to include or use transmitting a second beam of light, or adjusting a focal point of the second beam of light to a specific depth on the device under test.

Example 14 can include or use, or can optionally be combined with the subject matter of at least one of Examples 9-13 to include or use, wherein transmitting the first beam of light includes transmitting the first beam of light at a wavelength of between about 1150 and 1200 nanometers.

Example 15 can include or use, or can optionally be combined with the subject matter of at least one of Examples 9-14 to include or use, wherein transmitting the first beam of light includes transmitting the first beam of light at a power of about 200 milli-Watts or greater.

Example 16 can include or use, or can optionally be combined with the subject matter of at least one of Examples 9-15 to include or use filtering out a back reflection and a backscattering of light from light reflected off the device under test.

Example 17 can include or use subject matter (such as an apparatus, a method, a means for performing acts, or a device readable memory including instructions that, when performed by the device, can cause the device to perform acts), such as can include or use (1) a first light emitting element to transmit a first beam of light, (2) a polarized beam splitter to receive the transmitted first beam of light from the light emitting element and transmit light that is linearly polarized in a specific direction, (3) a quarter wave plate to receive the linearly polarized light from the beam splitter, circularly polarize light incident thereon by a quarter wavelength, transmit the circularly polarized light, (4) an XY stage, (5) a device under test situated on the XY stage, wherein the device under test is positioned in a path of the circularly polarized light, wherein the quarter wave plate is situated to receive light reflected from the device under test, linearly polarize the received light reflected from the device under test by another quarter wavelength to create half wavelength polarized light, and transmit the half wavelength polarized light, (6) a photo detector to receive half wavelength light transmitted by the quarter wave plate, or a controller electrically coupled to the first light emitting element to control a wavelength and power of the transmitted light from the first light emitting element, the controller electrically coupled to the XY stage to control the position of the device under test in the XY plane, the controller electrically coupled to the photo detector to receive image data from the photo detector.

Example 18 can include or use, or can optionally be combined with the subject matter of Example 17 to include or use a Z stage mechanically coupled to the XY stage, a lens exchanger mounted on the Z stage, or wherein the controller is electrically coupled to the Z stage to control a position of the lens exchanger in a Z-axis direction and the controller is electrically coupled to the lens exchanger to select an objective lens of the lens exchanger.

Example 19 can include or use, or can optionally be combined with the subject matter of at least one of Examples 17-18 to include or use a linear stage, a variable neutral density optical filter mounted on the linear stage, wherein the controller is configured to control the linear stage to position a specified optical density of the variable neutral density optical filter in a path of the half wavelength polarized light before the half wavelength polarized light is incident upon the photo detector.

Example 20 can include or use, or can optionally be combined with the subject matter of at least one of Examples 17-19 to include or use a second light emitting element configured to transmit a second beam of light, an optical offset element to focus the second beam of light on a surface of the device under test, an auto focus element situated to receive focused light from the optical offset element and focus the second beam of light at a specific depth in the device under test, or wherein the controller is electrically coupled to the second light emitting to control a wavelength and power of the second beam of light, electrically coupled to the optical offset element and the auto focus element to control the depth in the device under test that the auto focus element is focused on.

Example 21 can include or use, or can optionally be combined with the subject matter of at least one of Examples 17-20 to include or use, wherein the controller configures the first light emitting element to transmit the first beam of light at a wavelength of between about 1150 and 1200 nanometers.

Example 22 can include or use, or can optionally be combined with the subject matter of at least one of Examples 17-21 to include or use, wherein the controller configures the first light emitting element to transmit the first beam of light at a power of about 200 milli-Watts or greater.

The above detailed description includes references to the accompanying drawings, which form a part of the detailed description. The drawings show, by way of illustration, specific embodiments in which methods, apparatuses, and systems discussed herein can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

As used herein, a "-" (dash) used when referring to a reference number means "or", in the non-exclusive sense discussed in the previous paragraph, of all elements within the range indicated by the dash. For example, 103A-B means a nonexclusive "or" of the elements in the range {103A, 103B}, such that 103A-103B includes "103A but not 103B", "103B but not 103A", and "103A and 103B".

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:
1. An apparatus comprising:
a first light emitting element configured to transmit light with a wavelength and optical power configured to produce a reflected beam with at least one milli-Watt of power, wherein the wavelength of the light of the first light emitting element is one that passes through the die with less loss as compared to other wavelengths as determined by passing a broadband optical beam through bulk silicon and measuring the transmitted beam with an optical spectrum analyzer, and the optical power is set based on transmitting different optical intensity beams at the determined wavelength onto dies of varying thicknesses and measuring the transmitted power;

a polarized beam splitter to receive the transmitted light from the light emitting element and transmit light that is linearly polarized in a specific direction;

a collimator to receive the polarized light from the beam splitter and collimate the polarized light from the beam splitter to produce collimated polarized light;

a quarter wave plate to receive the collimated polarized light from the collimator, circularly polarize the light incident thereon by a quarter wavelength, transmit the quarter wavelength collimated polarized light, receive quarter wavelength polarized light reflected from a device under test, linearly polarize the received quarter wavelength polarized light by another quarter wavelength to create half wavelength polarized light, and transmit the half wavelength polarized light; and a photo detector to receive half wavelength light reflected from the device under test and transmitted by the quarter wave plate.

2. The apparatus of claim 1, wherein the collimator comprises a first front surface mirror mounted on a first galvanometer configured to oscillate the first front surface mirror in a first direction, a first lens to receive light from the first front surface mirror oscillating in the first direction and produced focused oscillating light, a second lens to receive the focused oscillating light and produce twice focused oscillating light, and a second front surface mirror to receive the twice focused oscillating light, the second front surface mirror mounted on a second galvanometer configured to oscillate the second front surface mirror in a second direction orthogonal to the first direction so that light incident thereon oscillates in the first and second directions.

3. The apparatus of claim 1, further comprising a variable optical density filter situated between the beam splitter and the photo detector, wherein the filter is situated on a stage configured to change the position of the optical density filter so as to selectively change an optical density of the filter in the path of the light from the beam splitter.

4. The apparatus of claim 1, further comprising:
a second light emitting element configured to transmit a second beam of light with an optical path independent of the first light emitting element;
an optical offset element to receive the second beam of light, create offset light, and direct the second beam of light to a specific depth in the device under test; and
an auto focus element configured to receive the second beam of light and focus the second beam of light at the specific depth in the device under test so as to illuminate the device under test at the specific depth using the auto focused second beam of light.

5. The apparatus of claim 1, wherein the first light emitting element is configured to transmit light at a wavelength of between about 1150 and 1200 nanometers.

6. The apparatus of claim 5, wherein the first light emitting element is configured to transmit light at a power of about 200 milli-Watts.

7. The apparatus of claim 1, further comprising an aperture situated between the beam splitter and the photo detector to filter out back reflection and backscattering of light from the device under test.

8. A method comprising:
determining a wavelength of light by passing a broadband optical beam through bulk silicon and measuring the transmitted beam with an optical spectrum analyzer through and choosing a wavelength that passes through the die with less loss as compared to other wavelengths;
determining an optical power based on transmitting different optical intensity beams at the determined wavelength onto dies of varying thicknesses and measuring the transmitted power;
transmitting a first beam of light at the determined wavelength and the determined optical power, the optical power configured to produce a reflected beam with at least one milli-Watt of power;
linearly polarizing the first beam of light in a specific direction;
circularly polarizing the linearly polarized light by a quarter wavelength to create circularly polarized light;
directing the circularly polarized light to a device under test;
linearly polarizing light reflected off the device under test by a quarter wavelength; and
creating an image of the linearly polarized light reflected off the device under test.

9. The method of claim 8, further comprising:
collimating the linearly polarized light before circularly polarizing the polarized light by a quarter wavelength.

10. The method of claim 9, wherein collimating the linearly polarized light includes oscillating the linearly polarized light in a first direction and oscillating the linearly polarized light in a second direction orthogonal to the first direction to oscillate the linearly polarized light in the first and second directions.

11. The method of claim 8, further comprising filtering the linearly polarized light reflected off the device under test using a variable neutral density filter before creating the image.

12. The method of claim 8, further comprising:
transmitting a second beam of light with an optical path independent of the first light emitting element;
optically offsetting the second beam of light and directing the second beam of light to a specific depth in the device under test; and
adjusting a focal point of the second beam of light to the specific depth on the device under test so as to illuminate the device under test at the specific depth using the auto focused second beam of light.

13. The method of claim 8, wherein transmitting the first beam of light includes transmitting the first beam of light at a wavelength of between about 1150 and 1200 nanometers.

14. The method of claim 13, wherein transmitting the first beam of light includes transmitting the first beam of light at a power of about 200 milli-Watts or greater.

15. The method of claim 8, further comprising filtering out a back reflection and a backscattering of light from light reflected off the device under test.

16. A system comprising:
a first light emitting element to transmit a first beam of light with a wavelength and optical power configured to produce a reflected beam with at least one milli-Watt of power, wherein the wavelength of the light of the first light emitting element is one that passes through the die with less loss as compared to other wavelengths as determined by passing a broadband optical beam through bulk silicon and measuring the transmitted beam with an optical spectrum analyzer, and the optical power is set based on transmitting different optical intensity beams at the determined wavelength onto dies of varying thicknesses and measuring the transmitted power;

a polarized beam splitter to receive the transmitted first beam of light from the light emitting element and transmit light that is linearly polarized in a specific direction;

a quarter wave plate to receive the linearly polarized light from the beam splitter, circularly polarize light incident thereon by a quarter wavelength, transmit the circularly polarized light;

an XY stage;

a device under test situated on the XY stage, wherein the device under test is positioned in a path of the circularly polarized light;

wherein the quarter wave plate is situated to receive light reflected from the device under test, linearly polarize the received light reflected from the device under test by another quarter wavelength to create half wavelength polarized light, and transmit the half wavelength polarized light;

a photo detector to receive half wavelength light transmitted by the quarter wave plate; and a controller electrically coupled to the first light emitting element to control a wavelength and power of the transmitted light from the first light emitting element, the controller electrically coupled to the XY stage to control the position of the device under test in the XY plane, the controller electrically coupled to the photo detector to receive image data from the photo detector.

17. The system of claim 16, further comprising:
a Z stage mechanically coupled to the XY stage;
a lens exchanger mounted on the Z stage; and
wherein the controller is electrically coupled to the Z stage to control a position of the lens exchanger in a Z-axis direction and the controller is electrically coupled to the lens exchanger to select an objective lens of the lens exchanger.

18. The system of claim 16, further comprising:
a linear stage;
a variable neutral density optical filter mounted on the linear stage;
wherein the controller is configured to control the linear stage to position a specified optical density of the variable neutral density optical filter in a path of the half wavelength polarized light before the half wavelength polarized light is incident upon the photo detector.

19. The system of claim 16, further comprising:
a second light emitting element configured to transmit a second beam of light with an optical path independent of the first light emitting element;
an optical offset element to focus the second beam of light on a surface of the device under test;
an auto focus element situated to receive focused light from the optical offset element and focus the second beam of light at a specific depth in the device under test; and
wherein the controller is electrically coupled to the second light emitting to control a wavelength and power of the second beam of light, electrically coupled to the optical offset element and the auto focus element to control the depth in the device under test that the auto focus element is focused on.

20. The system of claim 16, wherein the controller configures the first light emitting element to transmit the first beam of light at a wavelength of between about 1150 and 1200 nanometers.

21. The system of claim 16, wherein the controller configures the first light emitting element to transmit the first beam of light at a power of about 200 milli-Watts or greater.

* * * * *